United States Patent
Lilja et al.

(10) Patent No.: US 12,056,794 B2
(45) Date of Patent: Aug. 6, 2024

(54) SELF-CALIBRATION PROCEDURE FOR DIGITAL BREAST TOMOSYNTHESIS IMAGING APPARATUS

(71) Applicant: PLANMED OY, Helsinki (FI)

(72) Inventors: Mikko Lilja, Helsinki (FI); Juhamatti Malm, Helsinki (FI); Tarek Mohsen, Helsinki (FI)

(*) Notice: Subject to any disclaimer, the term of this patent is extended or adjusted under 35 U.S.C. 154(b) by 575 days.

(21) Appl. No.: 17/284,999

(22) PCT Filed: Sep. 16, 2019

(86) PCT No.: PCT/FI2019/050659
§ 371 (c)(1),
(2) Date: Apr. 13, 2021

(87) PCT Pub. No.: WO2020/053487
PCT Pub. Date: Mar. 19, 2020

(65) Prior Publication Data
US 2022/0139002 A1    May 5, 2022

(30) Foreign Application Priority Data
Sep. 14, 2018    (FI) .................................. 20180105

(51) Int. Cl.
G06K 9/00    (2022.01)
A61B 6/02    (2006.01)
G06T 11/00    (2006.01)

(52) U.S. Cl.
CPC ............. *G06T 11/005* (2013.01); *A61B 6/025* (2013.01); *G06T 2207/10004* (2013.01); *G06T 2207/10081* (2013.01); *G06T 2207/30068* (2013.01); *G06T 2211/436* (2013.01)

(58) Field of Classification Search
None
See application file for complete search history.

(56) References Cited

U.S. PATENT DOCUMENTS

| | | |
|---|---|---|
| 2004/0264648 A1 | 12/2004 | Claus et al. |
| 2005/0135664 A1 | 6/2005 | Kaufhold et al. |
| 2015/0305696 A1* | 10/2015 | Yamakawa ............ A61B 6/466 378/19 |
| 2017/0000451 A1 | 1/2017 | Aspelund et al. |

FOREIGN PATENT DOCUMENTS

JP    3639857 B2 *    4/2005    ............. A61B 6/025

* cited by examiner

Primary Examiner — Wei Wen Yang
(74) Attorney, Agent, or Firm — Lippes Mathias LLP (57) ABSTRACT

The invention relates to a calibration process specifically applicable for limited angle digital breast tomosynthesis (DBT). The method includes acquiring a set of X-ray projection exposure images, forming an initial estimate of the projection geometry corresponding to each of X-ray projection exposure images, computing an intermediate DBT reconstruction, establishing a set of rigid transformation parameters applied to an initial projection geometry estimate for each X-ray projection exposure image corresponding to calibration result, and computing a final DBT reconstruction using the set of X-ray projection exposure images and a final calibrated estimate of the projection geometry.

19 Claims, 5 Drawing Sheets

SELF-CALIBRATION PROCEDURE FOR DIGITAL BREAST TOMOSYNTHESIS IMAGING APPARATUS

FIELD OF INVENTION

The invention concerns projection geometry self-calibration and patient movement correction methods in the field of limited-angle digital breast tomosynthesis.

BACKGROUND OF INVENTION

The following disclosure relates to X-ray digital breast tomosynthesis, wherein a plurality of X-ray projection images acquired from a limited tomographic angle are used to reconstruct cross-sectional images of an anatomy of a patient. The duration of the X-ray projection image acquisition in limited angle tomography is typically of the order of ten seconds while the X-ray tube (X-ray source) and sensor (X-ray detector) physically travel the spatial trajectory corresponding to the limited acquisition angle.

The imaging trajectory should be known with a sufficient accuracy and the imaged object should remain sufficiently stationary during the X-ray projection image acquisition in order for the reconstructed image to be sharp and true to the anatomy, because the projection image measurements are assumed to represent co-registered integrated views of a stationary object. This results in a set of geometrically consistent measurements that can be used to reconstruct the attenuation distribution representing the studied anatomy. Whenever these assumptions are violated, the accuracy of the reconstructed image is degraded as a consequence of the projection measurements becoming mutually inconsistent.

The accuracy of the final image typically depends on how accurately the assumptions made in the reconstruction process correspond to the actual, physical image acquisition process. The estimated spatial positions of the X-ray source and detector corresponding to each acquired X-ray image affect the computation of the ray paths during the reconstruction process. Due to inherent manufacturing and operating tolerances, potential deformation of the imaging device and the patient leaning against the imaging device, the realized rotation angles and positions tend to deviate from the ideal values according to the assumed form of the imaging trajectory. A systematic deviation, however, can be addressed by using different calibration methods that are repeated after certain period of time or operation cycles.

Generally speaking, the most significant source of geometric inaccuracy is the potential movement of the patient during the acquisition of the X-ray projection images. In digital breast tomosynthesis, this is somewhat alleviated by virtue of the imaged anatomy (the breast) typically being physically compressed during the imaging. Nonetheless, if the imaged object moves during the acquisition of the X-ray projection images, the effective spatial paths of the ray measurements become mutually inconsistent. Although it is well-known that the patient should not move and the patients are routinely instructed not to do so, a patient typically cannot remain completely stationary during the acquisition of the X-ray projections. The patient may, for example, be startled by the sudden movement of, or sounds made by the imaging device.

The inaccuracies described above are typically present to some degree in all practical measurements. In a worst-case scenario, the resulting geometric inconsistency of the projection image measurements may even require repeating the scan after a radiologist has inspected the quality of the image reconstruction. This is undesirable due to the radiation dose associated with the X-ray image acquisition, which is aimed to be kept as low as reasonably possible.

Mammography is an X-ray imaging method widely used for breast cancer screening. In screening studies, mammography has been reported to achieve a sensitivity of 90-93% and a specificity of 90-97%. It has been estimated that mammography reduces breast cancer mortality by 35 percent among women over 50 and by 25-35 percent among women between 40 and 50 years of age.

Mammography images are examined for various anomalies in the breast such as calcifications, i.e. small deposits of calcium in the tissue.

A calcification generally cannot be detected by palpation, but it is visible in the X-ray image. Clusters of small calcium deposits, i.e. so-called microcalcifications, are an indication of increased breast cell activity, which may be associated with breast cancer.

In conventional mammography, the imaged breast gland is typically compressed between two compression plates and exposed to radiation at least twice, from above and from an oblique direction. If necessary, an additional third image is taken from the side. In the resulting two-dimensional X-ray radiographs, however, strongly attenuating tissues may obscure other structures lying on the same line-of-sight between the X-ray source and detector. This has led to applying also three-dimensional tomographic imaging in mammographic examinations, which requires acquiring X-ray exposure images from several angles.

Mammography can be performed using a three-dimensional tomosynthesis reconstruction process, where several two-dimensional X-ray projection images of a breast are acquired at different projection angles, e.g. in the range of ±15 degrees from the vertical axis, based on which one can reconstruct a tomographic image using well-known algorithms. Performing the reconstruction requires the availability of a sufficiently accurate representation of the three-dimensional projection geometry describing the relative positions of the X-ray source, detector, and the image grid used for the reconstruction.

As discussed, based on a number of two-dimensional X-ray projection images, a three-dimensional image can be reconstructed using suitable algorithms. Such imaging modality is commonly known as digital breast tomosynthesis imaging (DBT), in which a narrow, limited tomographic angle is used and a relatively small number of X-ray projection images is acquired, but in which on the other hand also a high in-plane spatial resolution is required for the detection of microcalcifications.

A typical modern digital mammography apparatus comprises a frame part and a C-arm or a corresponding structure that can be rotated with respect to the frame. The C-arm houses an X-ray source at one end and a radiation detector at the other end. The imaged breast is typically positioned close to the detector and compressed between plates for the duration of the X-ray exposure acquisition. The X-ray source is typically a relatively heavy component, which poses challenges to the mechanical design of a mammography imaging device. The relatively large mass favors an X-ray projection image acquisition strategy, where the C-arm moves continuously through its trajectory to avoid both mechanical vibrations resulting from the acceleration and deceleration of the C-arm as well as a prohibitively long duration of the X-ray exposures. This, however, requires short individual X-ray exposure times in the order of less than 50 milliseconds to avoid motion blurring of the exposures, and in turn using a sufficiently powerful X-ray source that further increases its mass and the related mechanical challenges.

In DBT imaging, where the dimensions of clinically relevant structures are extremely small, it is crucial to achieve a sufficiently accurate representation of the three-dimensional imaging geometry expressing the relative positions of the X-ray source and X-ray detector with respect to the image grid used for the tomosynthesis reconstruction. The spatial resolution of the reconstruction namely greatly depends on the consistency and accuracy of the imaging geometry used as an input for the reconstruction algorithm. This requires either a highly accurate mechanical design capable of accurately reproducing the nominal imaging trajectory, or a calibration method that allows routinely-preferably for each individual image acquisition-measuring or inferring the actual reproduced form of the X-ray source and detector trajectory with respect to the imaged field-of-view. Compared to CBCT imaging devices that typically rely on intermittently performed geometry calibration procedures, the on average lower retail prices of DBT imaging devices pose additional limitations to the viable mechanical accuracy of its moving parts, which then favors solutions that are based on continuously measuring or inferring the reproduced imaging geometry instead of relying on it to match a previous calibration procedure. Especially the prospective of upgrading an existing digital, mammography imaging device to enable DBT imaging without altering the core mechanical design is of both clinical and commercial interest. This further emphasizes the need for being able to observe the imaging geometry as it is being reproduced by the device.

Computational approaches have been developed to address the problem of geometric inaccuracy. In reported approaches in the literature, a virtual motion of the X-ray source and X-ray detector by means of a rigid geometric transformation in a fixed coordinate system has been applied to model and compensate for a rigid motion during the projection image acquisition. In recent approaches related to medical tomography imaging, such geometric transformation is optimized by maximizing the sharpness of the resulting reconstruction. Typically, such correction process is performed iteratively.

In DBT imaging, applying a fixed coordinate system for the modelling and compensation of geometric inconsistency or patient motion is not ideal, as the intrinsic geometric degrees-of-freedom are not separated by the coordinate system. In a DBT imaging device, it is particular that the X-ray beams diverge and form a pyramid-shaped cone. As a result, a shift along the isoray adjoining the X-ray source and the center of the X-ray detector will only affect the magnification factor, whereas an in-plane shift; along the X-ray detector's pixel array will result in a maximal shift of the imaged object within its projection image. Moreover, preventing a net transformation arising as a result of an applied geometric correction by known means of a rigid registration of the resulting corrected DBT reconstruction and the uncorrected DBT reconstruction is computationally expensive, especially if applied repeatedly during the geometric correction process.

Due to the requirement of high geometric accuracy in DBT imaging, dedicated approaches to ensure this have been devised. An example of these is embedding sufficiently radiopaque or radiolucent landmark objects in the field-of-view of the DBT imaging device. Based on the landmarks' positions in the X-ray projection images, it is possible to deduce the realized X-ray projection geometry and incorporate this information in the DBT image reconstruction process. However, the manufacturing costs of such precise embedded landmark assemblies are significant, their visibility requirement in the X-ray projection images limits the applicable field-of-view, and the resulting geometry representation cannot account for any movement of the patient with respect to the imaging device and the landmarks due to, e.g., discomfort, breathing or heartbeat despite the fact that the patient's breast remains compressed and mostly stationary during the X-ray projection image acquisition.

BRIEF DESCRIPTION OF INVENTION

In one embodiment of the disclosed process, a data-driven algorithm utilizing an intrinsic, rotating coordinate system attached to the spatial positions and orientation of the X-ray source and detector may be used to establish an improved estimate of the actual imaging geometry corresponding to the measured X-ray projection images. A net transformation in a fixed reference coordinate system is prevented by computing and subtracting the net transformation directly from the estimated corrective geometric transformation parameters. As a result, the relative positions of the X-ray source and detector system with respect to the patient, or vice versa, axe retrospectively estimated and improved based on the X-ray projection image contents. The purpose of the correction process is to improve the resulting image quality by improving the geometric consistency of the X-ray image measurements and, in turn, to better satisfy the requirements of image reconstruction. The intrinsic coordinate system enables defining the applied geometric degrees-of-freedom in a manner that corresponds to their relative importance to both the correction process as well as the resulting image quality.

The process may take as its input the data that is normally required for image reconstruction: a set of X-ray projection images and an estimate of the projection geometry corresponding to the spatial positions of the X-ray source and X-ray detector during the acquisition of the X-ray projection images. Similarly to corresponding methods, an intermediate reconstruction is first computed using the estimated projection geometry. Then, a corrective geometric transformation improving the geometric correspondence of each accessed X-ray projection image with the rest of the X-ray projection images is established with the transformation corresponding to a virtual movement of the X-ray source and detector during the image acquisition. In particular, a projection image-specific rotating coordinate system is applied for determining the corrective geometric transformation. The correction process, including the computation of an intermediate reconstruction using the current estimate of the projection geometry and the subsequent optimization of the corrective transformations, may be iterated for a number of times. After establishing the corrective geometric transformations, a final DBT reconstruction is computed using the X-ray projection images and the final estimate of the projection geometry corresponding to the corrective transformations.

In another embodiment, the object of the presented invention and its preferable embodiments is to enable three-dimensional tomosynthesis reconstruction from individual two-dimensional X-ray projection images taken by a digital mammography apparatus by determining the reproduced form of the imaging geometry retrospectively for each projection image in conjunction with the image reconstruction procedure. The invention enables achieving an accurate representation of the imaging geometry without resorting to landmark-based calibration procedures and furthermore enables utilizing an existing digital mammography device, whose mechanical precision is limited to its original intended use of 2D mammogram acquisition and cannot accurately reproduce a given X-ray exposure trajectory or in itself enable accurately measuring the position of the X-ray source and detector. Preferable embodiments of the invention thus include upgrading the software of an existing digital mammography apparatuses to be applicable also for three-dimensional tomosynthesis imaging.

In the invention, a self-calibration procedure is applied prior to the final DBT image reconstruction process. In the calibration procedure, a data-driven motion estimation algorithm is applied to establish a mutual geometric correspondence among the acquired X-ray projection images starting from an initial estimate of the projection geometry that reflects the approximate geometric form of the X-ray exposure trajectory. In essence, the positions of the X-ray source and detector with respect to the patient and the reconstructed image are retrospectively estimated based on the X-ray projection image data. Although in DBT imaging it is expected that the main source of geometric uncertainty and consistency among the X-ray projection images arises from the reproduction accuracy of the X-ray exposure acquisition trajectory, the approach is also capable of correcting for any patient movement that may occur despite the fact that the imaged breast is typically compressed during the imaging. Considering the high accuracy requirements associated with the small physical dimensions of the structures of interest, this is a distinct advantage over landmark assembly-based calibration approaches that can only capture the position of the X-ray source with respect to the X-ray detector but not the position of the patient.

The self-calibration procedure comprises measuring a set of digital mammography X-ray projection exposure images, transmitting the images to a reconstruction workstation, establishing an initial estimate of the projection geometry corresponding to each of X-ray projection exposure images, computing an intermediate DBT reconstruction and iteratively establishing a set of rigid transformation parameters for each X-ray projection exposure image to refine the initial projection geometry estimate. Applying the rigid transformation corresponds to a virtual motion of the X-ray source and detector, which brings them into correspondence with the actual, observed X-ray projection image contents. This is possible by using the measurement data itself for adaptively determining the imaging geometry.

The self-calibration procedure is preferably performed iteratively so that prior to each iteration an intermediate DBT image is reconstructed. Then, for each of the measured X-ray projection images, a digitally reconstructed radiograph (DRR) image is computed from the DBT reconstruction corresponding to each evaluated set of rigid transformation parameters. The validity of the transformation parameters, i.e. the validity of the candidate for virtual motion of the X-ray source and detector for the specific X-ray projection image, is established by measuring the similarity of the computed DRR image and the physically measured X-ray projection image. The optimization of the rigid transformation parameters is then based on finding the extremum of the similarity measure between the measured X-ray projection image and the corresponding computed DRR projection image as a function of the rigid transformation parameters. The procedure is iterated a number of times with the X-ray projection image-specific rigid transformation parameters used in the next iteration for computing the updated intermediate DBT reconstruction and further as the initial guess for the subsequent parameter optimization.

The benefits of the disclosed embodiments of the invention include an improvement in the projection geometric consistency, which results in a higher image quality in terms of sharpness, level of detail and contrast. A further benefit is that by potentially preventing a re-scan due to projection geometry-related image quality degradation, the radiation dose incurred to the patient may be decreased.

Concerning mammography, especially, the disclosed self-calibration process can be taken advantage of when wishing to upgrade an existing digital mammography imaging device to enable three-dimensional tomosynthesis imaging. Three-dimensional tomosynthesis increases the likelihood of early detection of breast cancer and can make tomosynthesis mammography apparatus more affordable. A further benefit is the possibility to correct not only mechanical inaccuracies but even slight patient movement during the projection image acquisition, which cannot be achieved when using e.g. fixed calibration landmark assemblies.

BRIEF DESCRIPTION OF FIGURES

The accompanying drawings provide further understanding of the disclosed patient movement correction method. In the drawings.

DETAILED DESCRIPTION OF INVENTION

A typical description of the imaging geometry consists of the 3D positions of the focus of the X-ray source and the center of the X-ray detector, and information to sufficiently uniquely determine the orientation of the X-ray detector. Such information may consist of e.g. rotation angles in a reference coordinate system that will determine the directions of the horizontal and vertical axes of the detector's pixel array. The projection geometry description is typically based on knowledge of the imaging device's physical measures as well as the ideal exposure trajectories corresponding to given imaging program. Furthermore, a periodic calibration process is typically performed to ensure a sufficient accuracy of the projection geometry.

A fundamental assumption employed in the reconstruction process is that the imaged anatomy has remained sufficiently stationary during the acquisition of the X-ray projection images. The rationale is that the X-ray projections should represent co-registered measurements of a stationary object that can then be consistently combined to reconstruct the structure of the object. A systematic error in the projection geometry can be compensated by a periodic calibration process, which eliminates the effects arising from any deviations from the assumed, ideal X-ray projection image acquisition trajectory.

A more difficult problem arises from patient movement during the imaging, which is unpredictable and random in its nature. Although it prevented to a degree by supporting the patient during the imaging, the relatively long duration of X-ray projection image acquisition in DBT imaging, of the order of 10 seconds, makes it unfeasible to completely eliminate patient movement. Moreover, elderly patients routinely participating in mammography examinations find it more difficult to remain still during the imaging.

In the event of significant patient movement during the X-ray projection image acquisition, pronounced streak-like or blurring artefacts will ensue in the reconstructed image, which may in a worst case render the image useless for the intended medical purpose. Repeating the scan may provide a better result but at the cost of additional radiation dose.

In the disclosed retrospective approach for compensating the adverse effects of undesired movements, an intermediate reconstruction is first computed using the 2D X-ray projection images and the estimated imaging geometry. It is sufficient to compute the intermediate reconstruction at a coarser resolution than is typically used when making reconstructions for diagnostic purposes. The intermediate reconstruction serves to aggregate the information from all X-ray projection images with the appearance of the reconstruction reflecting the mutual geometric consistency of the measured X-ray projection images.

The optimization of the projection-image-specific geometry is based on measuring the similarity of the physical X-ray projection images and the corresponding re-projected data of the intermediate reconstruction that forms a digitally reconstructed radiograph (DRR). The rationale is that when the estimated projection geometry is consistent, the reconstructed image that attempts, by definition, to satisfy the measurements conveyed by the projection images in the sense of the forward projection operation will yield reprojections that will closely match the measured data. In the event of a geometric mismatch, the reprojection of the intermediate reconstruction will deviate from the measured projection. As the intermediate reconstruction serves as an aggregate of all projection images, its reprojection reflects the sum of all projection images and the maximum similarity of the measured X-ray projection image and the forward projected images can be expected to be maximized when the corresponding reprojection geometry matches the average correct projection geometry of the intermediate reconstruction.

In a typical DBT imaging device, the emitted X-ray beams diverge and form a pyramid-shaped cone. A shift along the isoray adjoining the X-ray source and the center of the X-ray detector will only affect the magnification factor, whereas a shift along the X-ray detector plane will result in a maximal shift of the imaged object within its projection image. From this standpoint, the disclosed approach adopts a rotating coordinate system that is attached to the physical positions of the X-ray source and detector during the image acquisition. Namely by setting one axis to coincide with an isoray pointing from the X-ray source to the center of the X-ray detector's pixel array, and two other perpendicular axes to coincide with an orthogonal projection of the X-ray detector's pixel array axes to a plane that is perpendicular to the isoray. By limiting the geometric transformation of the projection geometry along these intrinsic axes for each projection image, it is possible to separate the geometric degrees-of-freedom, whose importance in the sense of the geometric accuracy varies.

When each X-ray projection image is subjected to an individual geometric transformation, it is possible that the resulting average transformation will incur a net effect on the reconstructed image. This manifests itself, e.g. as a global net shift or rotation of the reconstructed anatomy with respect to the uncorrected anatomy. It is possible that a net transformation of the anatomy will have adverse effects on the applicability of the reconstructed image. Thus, a compensation method for the net transformation is also disclosed. The net transformation can be estimated by mapping the transformation corresponding to each transformed projection image from the rotating coordinate system to the fixed coordinate system. For example, by assuming that each projection image is displaced only along its horizontal axis, the corresponding displacements in the fixed coordinate system can be computed based on the known horizontal axes of the projection-specific rotated coordinate systems, and the average value can be taken to represent the net displacement in the fixed coordinate system. By an inverse of the above-mentioned mapping, the inverse of the net transformation can be mapped back to the rotating coordinate systems and subtracted from the projection image-specific transformations. As a result, the net transformation in the fixed coordinate system is eliminated.

In the optimization process, the goodness of a corrective geometric transformation of a given X-ray projection image is measured by the similarity of the forward-projected image corresponding to the transformed projection geometry and the original X-ray projection image. The similarity of the reprojection and the X-ray projection can be measured, e.g. by the mean squared difference of the images, correlation coefficient, or gradient correlation coefficient. The optimal (in the sense of the similarity measure) geometric transformation for each projection image given an intermediate DBT reconstruction can then be determined by finding the extremum of the similarity measure between the forward-projected image and the X-ray projection image as a function of the parameters of the geometric transformation.

The optimization process then includes computing an intermediate DBT reconstruction using the initial estimate of the X-ray projection geometry; accessing all or a subset of the measured X-ray projection images; (for each accessed projection image) establishing a projection image-specific corrective transformation by finding the maximum similarity between the measured X-ray projection image and the corresponding forward projection of the intermediate reconstruction as a function of the parameters of the geometric transformation performed in the rotating coordinate system; estimating the net transformation in a fixed reference coordinate system and subtracting the corresponding transformation from the transformation parameters in the rotating coordinate system; computing a final reconstruction when a sufficient correction result is estimated to have been obtained.

Figure 1:
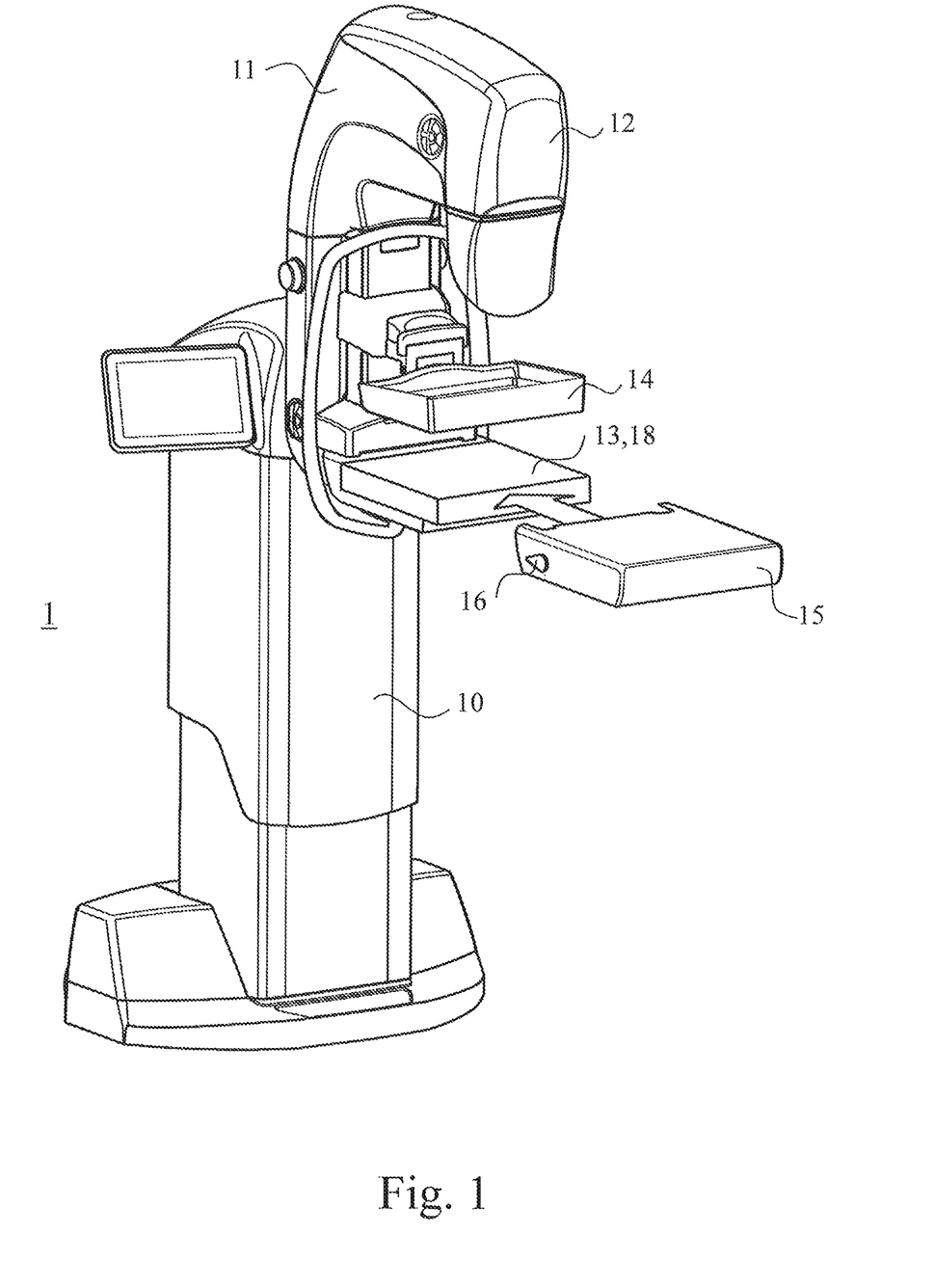
FIG. 1 shows an example of one typical mammography imaging apparatus.

FIG. 1 shows typical constructions of a digital mammography apparatus. The mammography apparatus (1) of FIG. 1 consists of a frame part (10) and a C-arm (11) (more commonly an arm structure (11)) attached to it. In the top part of the C-arm (11) inside its covers is arranged a source of X-ray radiation (12) which is arranged to generate an X-ray beam that passes through an upper compression plate (14) of the mammography apparatus (when such an upper compression plate is attached to the apparatus) and towards an X-ray detector (18) positioned in a detector housing (13). The detector housing (13) or a corresponding structure is typically arranged inside a lower tray structure (15) in which a grid structure (17) can be integrated to absorb radiation scattered by the imaged object. The lower tray structure (15) can be a fixed structure in the apparatus or it can be detachable. As the top surface of the lower tray structure (15) typically operates as a platform onto which the breast is positioned for imaging, this structure is also often called a lower compression plate. In the solution according to FIG. 1, the lower tray structure (15) is arranged with connecting means (16) to enable detachable connecting of the lower tray structure to the mammography apparatus (1).

A typical contemporary digital mammography apparatus is motorized so that the C-arm (11) can be displaced in the vertical direction and rotated around an axis that is typically the horizontal axis connecting the C-arm (11) to the frame (10) of the apparatus. The C-arm (11) can be implemented in two parts, whereby the basic construction of the apparatus can include either a substantially vertically standing frame part (10) or a frame part (10) that is fixed, e.g., to a wall or a ceiling and an arm structure (11) in connection with it, arranged to be rotatable relative to a horizontal rotation axis, out of the opposite ends of which arm structure (11) substantially at a first end is placed a radiation source (12) comprising a focus point and at a second end an image data receiving means (18). The arm structure (11) can be implemented such that it enables independent turning of the first end and/or the second end of the arm structure (11) relative to the horizontal rotation axis. The arrangement can further include control means which include an information recording means and a means for processing information related to the imaging, especially for processing image information.

Figure 2:
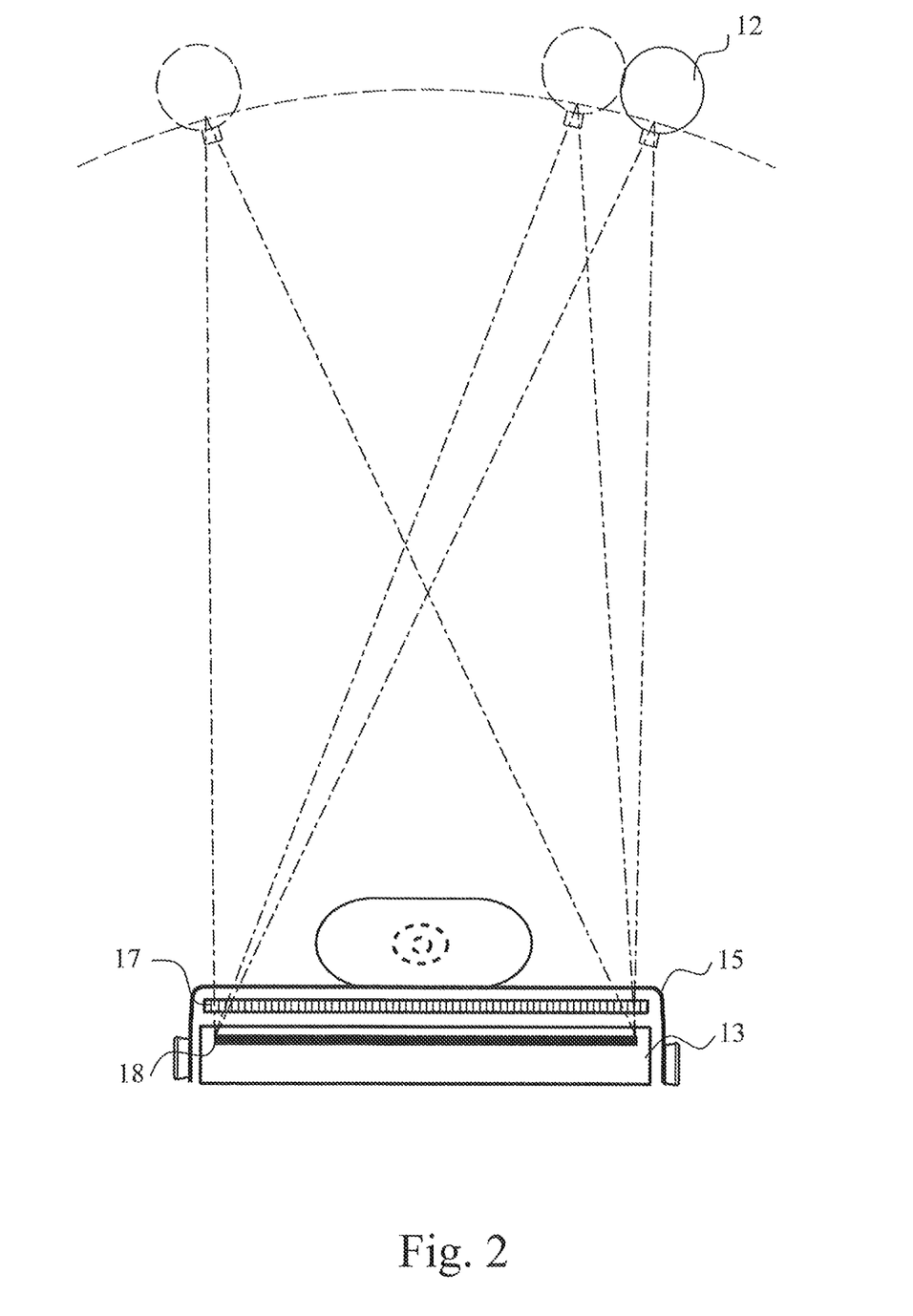
FIG. 2 shows the principle of typical tomosynthesis imaging.

FIG. 2 shows the principle of typical tomosynthesis imaging in which individual X-ray exposure images of a breast are taken at different projection angles, e.g. at the angle of about ±15 degrees from the vertical axis. FIG. 2 shows an arrangement in which only the position of the radiation source (12) with respect to the breast being imaged is deflected, but arrangements are also known, where the C-arm (11) is turned as a whole such that the breast is held positioned at its place but the detector (18) follows the movement of the radiation source (12) on the opposite side of the breast being imaged. The presented self-calibration method is applicable to either arrangement.

Figure 3:
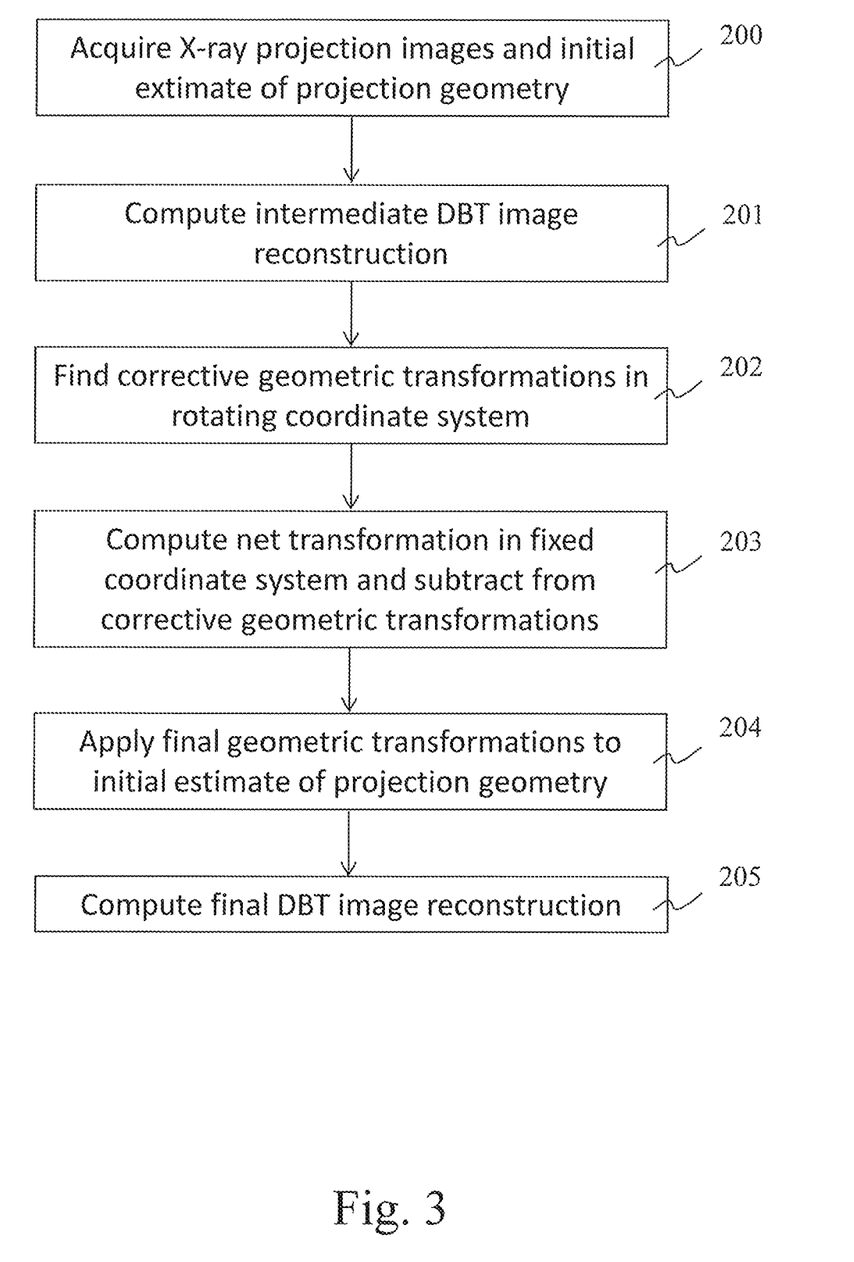
FIG. 3 shows as a flow chart one embodiment of a patient movement correction method.

FIG. 3 describes the steps of an embodiment of the invention for patient movement correction that may be used, for example, for processing images acquire by the imaging arrangement of FIG. 1. The method is based on finding corrective geometric transformations for the initially estimated projection geometry in a rotating coordinate system attached to the positions of the X-ray source 105 and X-ray detector 109.

In step 200 of the method of FIG. 3, the input data is acquired comprising the measured X-ray projection images and an initial estimate of the projection geometry corresponding to the acquisition process. The projection geometry determines the estimated orientation of the X-ray detector 109. The form of the projection geometry is typically based on a geometry calibration procedure utilizing e.g. a known reference phantom with radiopaque markers.

In step 201, an intermediate reconstruction for the purpose of the projection optimization method is computed using the input data acquired in step 200. It is possible to use downsampled versions of the input data, as it is typically not necessary to apply as high spatial resolution as in the images intended for diagnostic purposes. The intermediate reconstruction is understood to aggregate all available physical and, geometric information acquired during the measurement process in step 200. In the event of geometric inconsistency, this is reflected by the intermediate reconstruction by e.g. blurriness of the reconstructed details.

In step 202, corrective geometric transformations for the projection images are established in the rotating coordinate system. The purpose of the geometric transformations is to compensate for the intrinsic geometric inconsistency in the initial estimate of the projection geometry. The details of step 202 are explained below in reference to FIG. 4 but, more generally, the corrective geometric transformation is sought by finding the optimal geometric transformation. The goodness of a transformation is defined by assigning a similarity value to it. The similarity value is computed by comparing a re-projected digitally reconstructed radiograph (DRR) of the intermediate image reconstruction to the corresponding measured X-ray projection image, with the applied projection geometry corresponding to the evaluated geometric transformation. A higher similarity value is taken as an indication of a better corrective geometric transformation. Applying the rotating coordinate system for the geometric transformation enables separating the geometric degrees-of-freedom according to their significance to the problem in a cone-shaped projection geometry.

In step 203, the net geometric transformation in a fixed coordinate system is subtracted. The fixed coordinate system is defined typically in reference to static components of the imaging apparatus. The net geometric transformation is computed by linearly transforming the geometric transformations established in step 202 from the rotating coordinate system to the fixed coordinate system. The linear transformation is readily obtained based on the known coordinate axes of the rotated and fixed coordinate systems. After the net transformation has been established, its inverse is linearly transformed from the fixed coordinate system to its rotated coordinate system. The inverse of the net transformation then corresponds to a set of geometric transformation parameters for each projection image in the rotating coordinate system. Adding these values to the geometric parameter values established in step 202 will result in the net transformation being canceled out in the fixed coordinate system.

In step 204, the transformation parameter values resulting from step 203 are applied to the initial projection geometry estimate to obtain the corrected projection geometry estimate. In particular, steps 201-203 may be repeated iteratively a plurality of times before advancing to step 204.

In step 205, the final DBT reconstruction is computed using the corrected projection geometry estimate. The final reconstruction is computed in a normal manner with the exception to the situation where steps 201-204 were not applied that the initial projection geometry estimate is replaced by the corrected projection geometry estimate obtained in steps 201-204.

Figure 4:
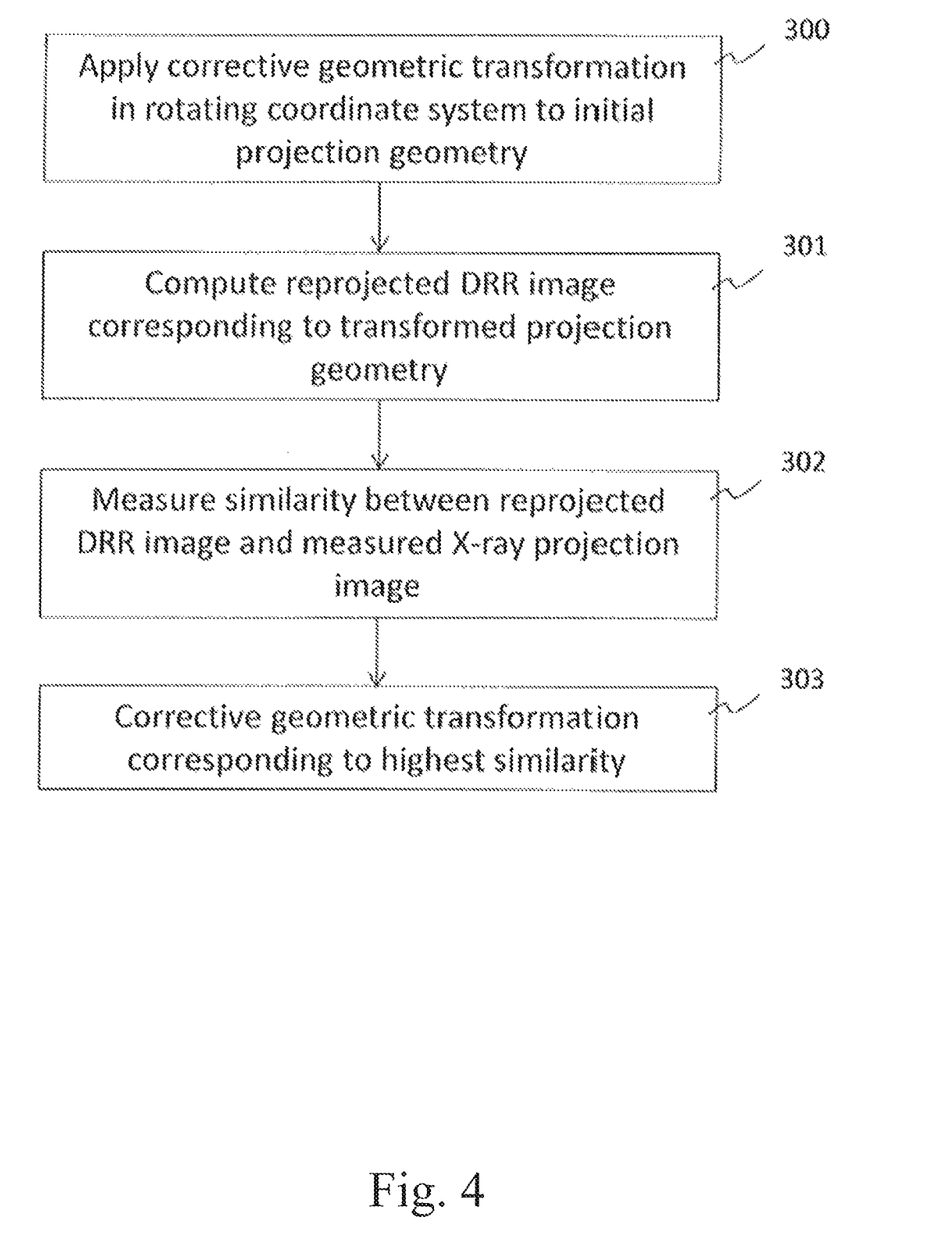
FIG. 4 shows a flow chart detailing the step 202 of FIG. 3.

FIG. 4 describes as an example details of step 202 according to FIG. 3. In step 300, the assessed geometric transformation is applied to the initial geometry of a projection image in the rotating coordinate system. Again, the coordinate system is defined to coincide with the spatial positions and orientation of the X-ray source and X-ray detector during the physical acquisition of the considered projection image.

Applying the transformation in the rotating frame of reference involves a linear mapping from the fixed coordinate system, where the imaging geometry is typically defined, to the rotating coordinate system, where the transformation is performed, followed by an inverse linear mapping from the rotating coordinate system to the fixed coordinate system. As a simple example of the accomplished effect, for applying a translation along an axis corresponding to the horizontal axis of the X-ray detector, namely its projection to a plane that is perpendicular to the isoray, the initial projection geometry of the projection image is mapped to the rotating coordinate system, translated along this axis of the rotating coordinate system by the given amount, which corresponds to a virtual movement of the X-ray source and detector, and then mapped back to the fixed coordinate system. The transformed projection geometry is expressed in the fixed coordinate system and the obtained transformed projection geometry is used as input for the subsequent step 301.

In step 301, a re-projected DRR image of the intermediate DST reconstruction computed in step 201 is computed using the transformed projection geometry obtained in step 300. The computation of the DRR image can be performed using a standard algorithm such as the Siddon raycasting method. In a typical reprojection algorithm, the input of the algorithm consists of the end points of the X-ray representation and the source image of which the DRR image is computed including knowledge of its spatial position and orientation expressed in the same coordinate system. In the described setting, this coordinate system corresponds to the fixed coordinate system. The effect of the geometric transformation applied in step 300 is to change the end points of each virtual X-ray path through the intermediate reconstruction, which propagates the effect of the geometric transformation to the obtained DRR image.

In step 302, the similarity between the DRR image obtained in step 301 and the X-ray projection image acquired in step 200 is evaluated. The similarity is based on a pointwise comparison of the images using established approaches such as the average squared difference of the images or their cross-correlation. The specific measure used for evaluating the similarity is not significant to the described method.

The obtained similarity value is assigned to the geometric parameters given as input to step 300. A higher similarity is taken as an indication of more suitable geometric transformation parameters.

In step 303, the optimal geometric transformation parameters are established by finding the parameters corresponding to the highest similarity value obtained by applying steps 300-302. In a typical setting, steps 300-302 are repeatedly evaluated by a suitable minimization algorithm such as the well-known Nelder-Mead simplex algorithm to establish the optimal geometric transformation parameters. These parameters are stored and assigned to the specific projection image until they are potentially changed by a repetition of steps 201-203.

Figure 5:
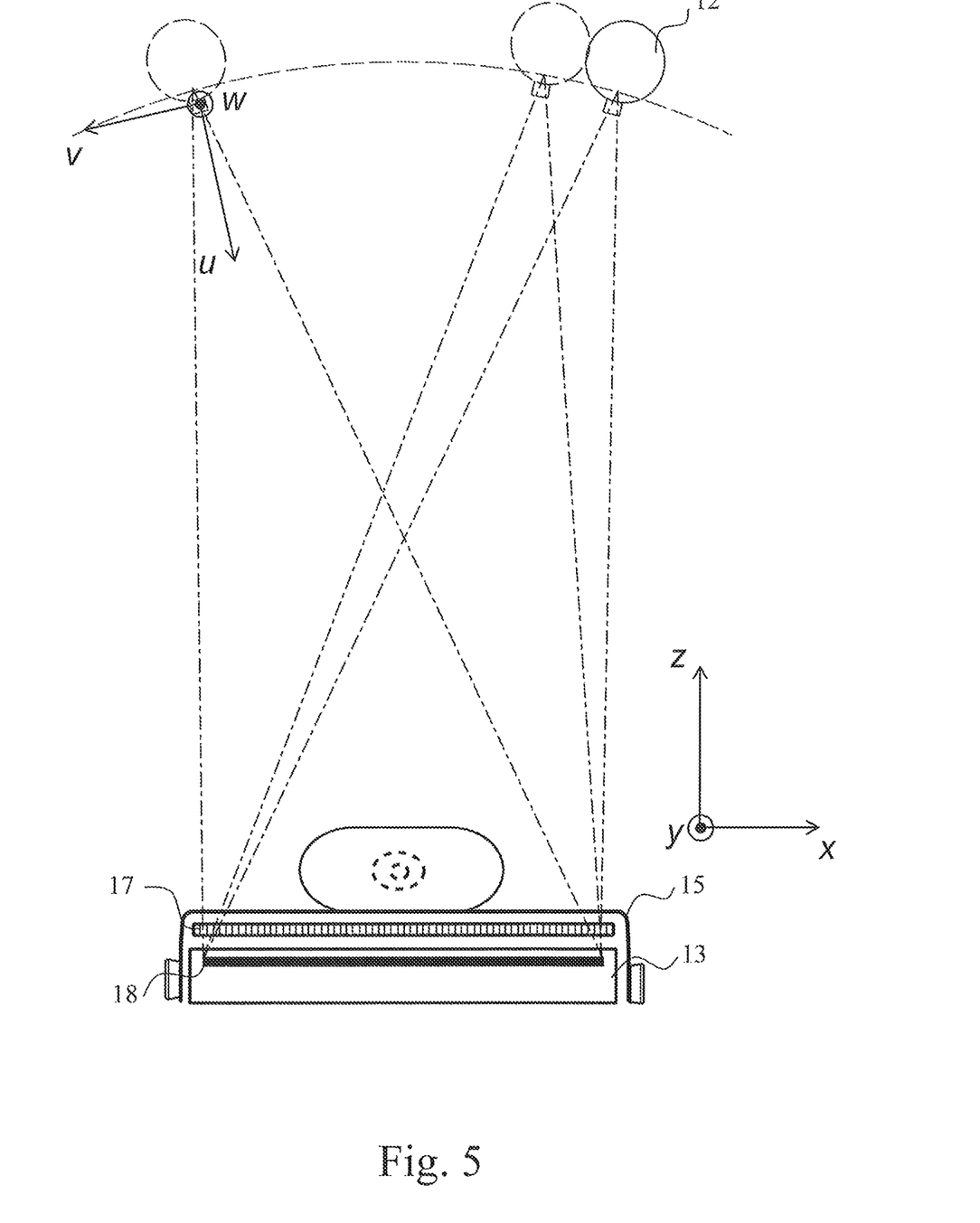
FIG. 5 illustrates the fixed and rotating coordinate systems in the context of tomosynthesis imaging.

FIG. 5 illustrates the rotating coordinate system applied in step 202. In a DBT imaging apparatus, an arm structure (11) like the one shown in FIG. 1 typically supports the X-ray source (12) and X-ray detector (18). In DBT imaging, it is particular that the X-ray beams diverge and form a pyramid-shaped cone. A shift along the isoray adjoining the X-ray source (12) and the center of the X-ray detector (18) will only affect the magnification factor, whereas a shift corresponding to the axes of the X-ray detector's pixel array will result in a maximal shift of the imaged object within its projection image. From this standpoint, the disclosed approach adopts a rotating uvw coordinate system that is attached to the physical positions and orientations of the X-ray source during the image acquisition. By limiting the geometric transformation of the projection geometry along these intrinsic axes for each projection image, it is possible to separate the geometric degrees-of-freedom, whose importance in the sense of the geometric accuracy varies. The fixed coordinate system, where the net transformation is computed is denoted by the xyz coordinate system.

Setting the u axis of the coordinate system to coincide with the isoray pointing from the X-ray source (12) to the center of the X-ray detector (18) and the v axis with the planar projection of the horizontal axis of the X-ray detector's (18) pixel array to a plane that is perpendicular to the isoray, these degrees-of-freedom are, for example, for a rigid transformation:

1. Longitudinal shift along the isoray (u axis); 2. Lateral shift along the projected horizontal axis of the X-ray detector's pixel array (v axis); 3. Vertical shift along the projected vertical axis of the X-ray detector's pixel array (w axis); 4. Rotation around the u axis (roll angle); 5. Rotation around the v axis (pitch angle); 6. Rotation around the w axis (yaw angle).

The result of the disclosed patient movement correction method is an improved estimate of the projection geometry corresponding to the physical acquisition of the X-ray projection images and correspondingly a DBT reconstruction image, where the effect of geometric inconsistency has been reduced.

The preferable embodiments of the invention include a mammography imaging arrangement for tomosynthesis including a mammography imaging apparatus (1) that includes either a substantially vertically standing frame part (10) or a frame part (10) that can be fixed to a wall or a ceiling, an arm structure (11) in connection with said frame part (10) which is rotatable relative to a horizontal rotation axis, wherein out of the opposite ends of said arm structure (11) substantially at the first end is placed an X-radiation source (12) comprising a focus point and substantially at the second end an image data receiving means (18). In connection with said second end of the arm structure (11) is additionally arranged a lower tray structure (15) which positions substantially on top of the image data receiving means (18). The arrangement also includes control means for moving at least one component of the arm structure (11) and for controlling operation of the image data receiving means (18) as well as processing means which include an information recording means and a means for processing information.

A tomosynthesis imaging process can start by positioning the patient for imaging, which in connection with the arrangement above means placing a breast on top of the lower tray structure (15) and possibly compressing it to be immovable by the upper compression plate (14). If the arm structure (11) of the apparatus, or the part of the arm structure comprising the radiation source (12), has not already been driven to the first projection angle of the imaging process, it will be driven there, after which the arrangement is ready for the first exposure. Image information detected by the detector (18) in connection with the exposure is read to record and the imaging is repeated at small projection angle intervals, e.g. at projection angle intervals of 2 degrees.

The measured raw data corresponding to the X-ray exposures typically represents the intensity or a proportional measure of the incident X-ray radiation. A well-known logarithmic mapping is applied to the measured raw images to arrive at X-ray projection images that are approximately proportional to spatial pencil integrals of the total X-ray attenuation distribution of the imaged breast. The preprocessing of the measured X-ray exposure images may be arranged to be performed on the imaging apparatus or on an image processing workstation.

After acquiring and transmitting the preprocessed X-ray projection images to an image processing workstation or comparable, an iterative procedure for determining the imaging geometry for each X-ray exposure is executed. If the X-ray detector is fixed, the imaging geometry is determined by the 3D position of the X-ray source with respect to the detector. If the detector moves slightly in the course of the X-ray exposure acquisition, also the position of the detector is needed to fix the imaging geometry. This is also required for correcting for any patient movement and is assumed in the following. The projection geometry description therefore comprises the X-ray source (focal point) and detector positions and the attitude of the detector. The X-ray source positions are expressed as points in a 3D reference coordinate system.

In the iterative procedure, the three-dimensional positions of the X-ray radiation source (12) and detector (18) corresponding to the exposure of each X-ray projection image are estimated by using predetermined estimates of their positions as an initial guess and then optimizing a corrective rigid transformation resulting in refined estimates that maximize the geometric correspondence between each measured X-ray projection image and all other measured X-ray projection images. It is understood that due to the aforementioned aspects related to the limited mechanical and positional precision of digital mammography devices, the initial estimate of the X-ray source positions is practically always non-ideal.

The geometric correspondence of each X-ray projection image with all other X-ray projection images is measured by comparing it to the corresponding digitally reconstructed radiograph (DRR) computed from an intermediate DBT image reconstruction using a suitable forward projection algorithm. The DBT reconstruction can be computed using a suitable algorithm such as the well-known iterative SIRT algorithm. It is understood that in an ideal situation, where the projection geometry would be exactly known and an ideal image reconstruction could be computed from ideal projection image measurements with infinite accuracy, e.g., in terms of the image element size and the physical model for the X-ray propagation and detection, the computed DRR images would be exactly equivalent to the measured X-ray projection images. Furthermore, the intermediate DBT reconstruction is understood to essentially contain all available structural and geometric information from each X-ray projection image. Based on this reasoning, an iterative approach is adopted to incrementally estimate the imaging geometry that maximizes the correspondence between the measured X-ray projection image and computed DRR projection images of an intermediate tomosynthesis reconstruction. The intermediate DBT reconstruction is typically computed on a coarser sampling than a typical DBT image reconstruction used for medical diagnosis would be. This is clone for improving the computational efficiency of the motion correction algorithm used in the self-calibration process.

The rigid transformation parameters of the projection geometry description for each X-ray projection image are initialized to an identity transformation that leaves the initial projection geometry description unaltered. For each iteration and for each X-ray projection image, updated rigid transformation parameters are established that maximize the geometric correspondence between the measured projection image and the corresponding computed DRR projection image of the intermediate DBT reconstruction. The level of correspondence and in turn the suitability of each rigid transformation candidate is then measured by a similarity measure computed from the measured X-ray projection image and the computed DRR projection image.

To summarize, steps 300-304 describe the iterative optimization of the projection-specific rigid transformation parameters in the self-calibration procedure with each individual iteration consisting of these steps. Each iteration begins by computing an intermediate DBT reconstruction using the measured X-ray projection images and the current estimates of the imaging geometry as given by its initial estimate and the projection-specific rigid transformation parameters that uniquely determine the altered form of the imaging geometry, step 300. In the first iteration, the transformation parameters are set to identity transformation, i.e. zero translation or rotation.

The validity of new candidate values for the rigid transformation parameters of each X-ray image's projection geometry in each iteration is assessed by first computing the corresponding DRR projection image of the current intermediate DBT reconstruction. The computation of the DRR projection image begins by applying the candidate rigid transformation parameters to the initial estimate of the current projection image's projection geometry, step 301. The rigid transformation is applied to the X-ray source and detector positions, which are then used to compute the DRR projection image.

With the candidate rigid transformation applied to the projection geometry of the current X-ray projection image, a DRR image of the current intermediate DBT reconstruction is computed using a suitable forward projection algorithm, step 302. The resulting DRR image is uniquely determined by the DBT reconstruction and the projection geometry resulting by applying the rigid transformation parameters to the original initial projection geometry estimate.

The validity of the candidate values for the rigid transformation parameters is estimated by evaluating the similarity of the measured X-ray projection image and the DRR projection image computed using the projection geometry resulting from applying the said transformation parameters, step 303. The similarity is evaluated by computing a suitable image similarity measure such as image cross-correlation, gradient correlation, mutual information, or entropy of the image difference. A higher similarity between the measured X-ray projection image and the computed DRR image is taken as an indication or more suitable rigid transformation parameters by virtue of the aforementioned considerations.

The optimization of the rigid transformation parameters is performed by finding the extremum of the applied similarity measure between the measured X-ray projection image and the computed DRR projection image as a function of the rigid transformation parameters, step 304. The optimization is performed by iterating steps 301-303 until a predetermined condition is met. The predetermined condition may be, for example, a number of iteration cycles or an overall change in the projection-specific transformation parameters. After the optimal rigid transformation parameters corresponding to the found extremum of the projection similarity measure are found, the transformation parameters are stored to be used in the subsequent iteration again starting from step 300. The sufficient number of iterations is typically dependent on the desired level of accuracy of the correction procedure and the accuracy of the initial estimate. One may expect that the iterative process converges to a point, where the projection geometry estimate does not significantly change anymore between the subsequent iterations, and the computation may be stopped.

The sole result of the motion correction based self-calibration process is a set of projection image-specific rigid transformation parameters that, applied to the initial projection geometry estimate, result in an optimized estimate of the X-ray projection geometry. The optimized projection geometry estimate replaces the initial projection geometry estimate and it is used as an input for the computation of the final DBT reconstruction image representing the patient that is used for medical purposes.

In the context of tomosynthesis in mammography, the invention may be used with limited number of projection images and using a limited tomographic angle. The number of projection images may be only in the order of tens of images, such as less than 20 images or even less than 10 images. The tomographic angle may be less than about 60 degrees, or even less than 40 degrees, such as 15-30 degrees.

The above-mentioned method may be implemented as computer software which is executed in a computing device. When the software is executed in a computing device it is configured to perform the above described inventive method. The software is embodied one computer readable medium so that it can be provided to the computing device.

The disclosed method may be implemented as computer software executed in a computing device. The software is embodied on a computer readable medium so that it can be provided to the computing device.

As stated above, the components of the exemplary embodiments can include computer readable medium or memories for holding instructions programmed according to the teachings of the present embodiments and for holding data structures, tables, records, and/or other data described herein. Computer readable medium can include any suitable medium that participates in providing instructions to a processor for execution. Common forms of computer-readable media can include, for example, a floppy disk, a flexible disk, hard disk, magnetic tape, any other suitable magnetic medium, a CD-ROM, CD±R, CD±RW, DVD, DVD-RAM, DVD±RW, DVD±R, HD DVD, HD DVD-R, HD DVD-RW, HD DVD-RAM, Blu-ray Disc, any other suitable optical, medium, a RAM, a PROM, an EPROM, a FLASH-EPROM, any other suitable memory chip or cartridge, a carrier wave or any other suitable medium from which a computer can read.

To summarize, embodiments of the invention include a self-calibration process for digital breast tomosynthesis reconstruction, comprising;
- acquiring a set of X-ray projection images of the imaged patient comprising a limited number of two-dimensional, images over a limited tomographic angle using an X-ray imaging means containing an X-ray source and X-ray detector;
- defining an initial projection geometry estimate describing the spatial positions and orientation of the X-ray source and the X-ray detector during the acquisition of the X-ray projection images;
- computing an intermediate DBT reconstruction using the X-ray projection images and the initial projection geometry estimate;
- determining projection-image-specific corrective geometric transformations for the initial projection geometry estimate based on the X-ray projection images, the initial projection geometry estimate, and the intermediate DBT reconstruction;
- and computing a final DBT reconstruction using the X-ray projection images and a corrected estimate of the projection geometry corresponding to the determined corrective geometric transformations, wherein the corrective geometric transformations for the initial projection geometry estimate are determined in a projection-image-specific rotating coordinate system corresponding to the spatial positions and orientations of the X-ray source and X-ray detector during the acquisition of the X-ray projection images.

Said projection-image-specific rotating coordinate system can be defined by setting one axis to coincide with an isoray pointing from the X-ray source to the center of the X-ray detector's pixel array, and two other perpendicular axes to coincide with an orthogonal projection of the X-ray detector's pixel array axes to a plane that is perpendicular to the isoray.

Another possibility for defining the projection-image-specific rotating coordinate system is to set two perpendicular axes to coincide with the X-ray detector's pixel array and third perpendicular axis to coincide with the normal of the X-ray detector's pixel array.

According to one embodiment, the projection-image-specific rotating coordinate system can be defined by setting two perpendicular axes to coincide with the orthogonal geometric projections of the X-ray detector's edges to a plane that is perpendicular to the isoray and the third axis to coincide with the isoray.

According to one embodiment, the projection-image-specific rotating coordinate system can be defined by setting two perpendicular axes to coincide with the X-ray detector's edges and the third axis to coincide with the normal of the X-ray detector.

The projection geometry of the re-projected digitally reconstructed radiograph is obtained by applying a geometric transformation in the rotating coordinate system to the initial projection geometry estimate.

The corrective geometric transformations are determined by finding the maximal similarity between the X-ray projection images and corresponding re-projected digitally reconstructed radiographs of the intermediate DBT reconstruction.

A net transformation in a fixed coordinate system is computed and subtracted from the corrective geometric transformations determined in a rotating coordinate system.

The net transformation in the fixed coordinate system is computed by mapping the projection-image-specific geometric transformations from the rotating coordinate system to a fixed coordinate system and taking their average, and the average subtracted from the geometric transformations after a mapping from the fixed coordinate system to the rotating coordinate system.

The computation of the intermediate DBT reconstruction and determining the corrective geometric transformations are iterated a plurality of times, with the corrected projection geometry estimate after each iteration acting as a new initial projection geometry estimate for the following iteration, and the final corrected projection geometry estimate corresponding to the corrected projection geometry estimate of the last applied iteration.

The embodiments include a computer program comprising computer program code that is configured to perform a method according to what is disclosed above, when executed in a computing device, and an apparatus comprising:
- at least one processor configured to execute computer programs; and
- at least one memory configured to store computer programs and the related data;
- wherein the apparatus is connectable to a medical imaging apparatus and configured to perform a method according what was disclosed above.

One further embodiment is a method for a digital breast tomosynthesis (DBT) self-calibration process comprising:
- acquiring a set of X-ray projection exposure images;

forming an initial estimate of the projection geometry corresponding to each of X-ray projection exposure images; and further computing an intermediate DBT reconstruction; and establishing a set of rigid transformation parameters applied to the initial projection geometry estimate for each X-ray projection exposure image corresponding to the calibration result;

computing a final DBT reconstruction using the set of X-ray projection exposure images and a final calibrated estimate of the projection geometry.

The final DBT reconstruction image is computed using the original X-ray exposures and a refined projection geometry estimate based on an established set of rigid transformation parameters.

The method further comprises performing a projection image-specific rigid transformation of the initial projection geometry estimate by applying an established set of rigid transformation parameters.

The transformation comprises translation and rotation.

The set of rigid transformation parameters applied to the current projection geometry estimate for a given projection image results in an altered or refined form of the projection geometry corresponding to a virtual motion of the X-ray source and detector.

Computing a DRR image of the intermediate DBT reconstruction is preceded by a rigid transformation to the corresponding initial projection geometry estimate.

The method further comprises performing the rigid transformation in a projection image-specific rotating coordinate frame.

The method further comprises measuring the similarity of the computed DRR image and the corresponding measured X-ray projection image.

The method further comprises optimizing the projection-specific rigid transformation parameters by finding the extremum of the similarity measure between the measured X-ray projection image and the computed DRR projection image as a function of the rigid transformation parameters.

The method is iterated a plurality of times and the transformation parameters are used in the next iteration then as the initial guess for the subsequent parameter optimization.

In one embodiment, a computer program comprises computer program code that is configured to perform a method according what was discussed above when executed in a computing device.

One embodiment is an apparatus comprising:
at least one processor (112) configured to execute computer programs; and
at least one memory (113) configured to store computer programs and the related data;
wherein the apparatus is connectable to a medical imaging arrangement and configured to perform a method as discussed above.

Another embodiment is a medical digital breast tomosynthesis imaging arrangement comprising:
a medical imaging device; and
an apparatus as disclosed above, wherein the apparatus is connected with the medical imaging device.

It is obvious to a person skilled in the art that with the advancement of technology, the basic idea of the self-calibrating medical imaging apparatus may be implemented in various ways. The self-calibrating medical imaging apparatus and its embodiments are thus not limited to the examples described above; instead they may vary within the scope of the claims.

The invention claimed is:

1. Self-calibration process for digital breast tomosynthesis (DBT) reconstruction, comprising:
acquiring a plurality of two-dimensional X-ray projection images over a limited tomographic angle using an X-ray imaging means containing an X-ray source and X-ray detector;
defining an initial projection geometry estimate describing the spatial positions and orientation of the X-ray source and the X-ray detector during the acquisition of said X-ray projection images;
computing an intermediate DBT reconstruction using the X-ray projection images and the initial projection geometry estimate;
determining projection-image-specific corrective rigid geometric transformations for the initial projection geometry estimate based on the X-ray projection images, the initial projection geometry estimate, and the intermediate DBT reconstruction;
and computing a final DBT reconstruction using the X-ray projection images and a corrected estimate of the projection geometry corresponding to the determined corrective rigid geometric transformations,
wherein said X-ray projection images comprise a limited number of two-dimensional images acquired over a limited tomographic angle, and the corrective rigid geometric transformations for the initial projection geometry estimate are determined in a projection image specific rotating coordinate system corresponding to the spatial positions and orientations of the X-ray source and X-ray detector during the acquisition of the X-ray projection images, wherein the corrective rigid geometric transformations are determined by finding the maximal similarity between the X-ray projection images and corresponding re-projected digitally reconstructed radiographs of the intermediate DBT reconstruction.

2. The process according to claim 1, wherein said projection-image-specific rotating coordinate system is defined by setting one axis to coincide with an isoray adjoining the X-ray Source and center of the X-ray detector's pixel array, and two other perpendicular axes to coincide with an orthogonal projection of the X-ray detector's pixel array axes to a plane that is perpendicular to the isoray.

3. The process according to claim 1, wherein said projection-image-specific rotating coordinate system is defined by setting two perpendicular axes to coincide with the X-ray detector's pixel array and a third perpendicular axis to coincide with a normal of the X-ray detector's pixel array.

4. The process according to claim 1, wherein the projection geometry of a re-projected digitally reconstructed radiograph is obtained by applying the corrective rigid geometric transformation in the rotating coordinate system to the initial projection geometry estimate.

5. The process according to claim 1, wherein a net transformation in a fixed coordinate system is from the corrective rigid geometric transformations determined in the rotating coordinate system.

6. The process according to claim 5, wherein the net transformation in the fixed coordinate system is computed by mapping corrective rigid geometric transformations from the rotating coordinate system to the fixed coordinate system and taking their average, and the average, subtracted from the corrective rigid geometric transformations after a mapping from the fixed coordinate system to the rotating coordinate system.

7. The process according to claim 6, wherein the computation of the intermediate DBT reconstruction and determining the corrective rigid geometric transformations are iterated a plurality of times, with the corrected projection geometry estimate after each iteration acting as a new initial projection geometry estimate for the following iteration, and the final corrected projection geometry estimate corresponding to the corrected projection geometry estimate of the last applied iteration.

8. The process according to claim 1, wherein said limited number of projection images is of the order of tens of images.

9. The process according to claim 1, wherein said limited number of projection images is less than 20 images.

10. The process according to claim 1, wherein said limited number of projection images is less than 10 images.

11. The process according to claim 10, wherein said limited tomographic angle is less than about 60 degrees.

12. The process according to claim 10, wherein said limited tomographic angle is less than about 40 degrees.

13. A medical digital breast tomosynthesis imaging arrangement comprising:
a medical imaging device; and
at least one processor configured to execute a computer program, and at least one memory configured to store the computer program, wherein the computer program comprises a computer program code that is configured to perform the process according to claim 1 when executed by the at least one processor.

14. A method for a digital breast tomosynthesis (DBT) self-calibration process comprising:
acquiring a set of X-ray projection exposure images over a limited tomographic angle;
forming an initial estimate of the projection geometry corresponding to the set of X-ray projection exposure images;
characterized in that the method further comprises;
computing an intermediate DBT reconstruction using the set of X-ray projection exposure images and the initial estimate; and
establishing a set of rigid transformation geometric parameters applied to the initial estimate of the projection geometry; and
computing a final DBT reconstruction using the set of X-ray projection exposure images and a final calibrated estimate of the projection geometry, wherein the final DBT reconstruction image is computed using the original X-ray exposures and a refined projection geometry estimate based on the established set of rigid transformation geometric parameters, and wherein the corrective rigid transformation geometric parameters are determined by finding the maximal similarity between the X-ray projection exposure images and corresponding re-projected digitally reconstructed radiographs of the intermediate DBT reconstruction.

15. The method according to claim 14, wherein the method further comprises performing a projection image-specific rigid transformation of the initial projection geometry estimate by applying an established set of rigid transformation parameters.

16. The method according to claim 14, wherein the set of rigid transformation parameters applied to the current projection geometry estimate for a given projection image results in an altered or refined form of the projection geometry corresponding to a virtual motion of the X-ray source and detector.

17. The method according to claim 16, wherein the method further comprises performing the rigid transformation in a projection image-specific rotating coordinate frame.

18. The method according to claim 16, wherein the method further comprises measuring the similarity of the computed image and the corresponding measured X-ray projection image.

19. The method according to claim 16, wherein the method further comprises optimizing the projection-specific rigid transformation parameters by finding the extremum of similarity measure between the measured X-ray projection image and the computed image as a function of the rigid transformation parameters.

* * * * *